United States Patent [19]

Barberet-Maiolino et al.

[11] Patent Number: Plant 7,047

[45] Date of Patent: Oct. 17, 1989

[54] SPRAY CARNATION NAMED LONBANKIR

[75] Inventors: Nicole Barberet-Maiolino; Henri Blanc, both of Antibes, France

[73] Assignee: Establissements Barberat et Blanc, Laboratoire de Physiologie Vegetale, Les-Maures, France

[21] Appl. No.: 255,483

[22] Filed: Oct. 11, 1988

[51] Int. Cl.[4] ..... A01H 5/00

[52] U.S. Cl. ..... Plt./71

[58] Field of Search ..... Plt. 71

*Primary Examiner*—Robert E. Bagwill

*Attorney, Agent, or Firm*—Charles W. Rummler

[57] ABSTRACT

A new cultivar of spray carnation particularly distinguished by the medium sized, well formed flowers of a light purple coloration produced profusely in the Spring, midseason and Fall, the plant being very branched with a vigorous, upright growth habit and very abundant foliage; the plant is also very resistant to *Fusarium oxysporum.*

1 Drawing Sheet

BACKGROUND OF THE NEW PLANT

This new variety of spray carnation originated as a seedling of a hybrid resulting from our crossing of selected carnation varieties from our collection of carnation plants maintained at our nursery at 83250 La Londe-Les-Maures, France, our objective being to develop a spray carnation having nice color, excellent quality and a strong resistance to *Fusarium oxysporum.* This particular seedling was selected for propagation because of the pleasing color of its flower and the excellent quality of its growth. The selected plant was propagated by us at La Londe by means of cuttings with such pleasing results that propagation was continued through several successive generations by cuttings of successive plants, which demonstrated conclusively that the novel characteristics of the selected seedling were fully retained from generation to generation and appeared to be firmly fixed. Present propagation of this new spray carnation is done at La Londe both by cuttings and by in vitro propagation methods.

DESCRIPTION OF THE DRAWING

Our new variety of spray carnation is illustrated by the accompanying drawing, which shows several blooming stems bearing flowers in several stages of development, including a face view of a mature bloom, the colors shown being as nearly true to those herein specified as is reasonably possible to obtain by professional photographic procedures.

DESCRIPTION OF THE NEW PLANT

The following is a detailed description of our new variety of spray carnation plant made by observation of plants grown, both under glass and outdoors, at our nursery at La Londe, with color designations according to The R.H.S. Colour Chart published by The Royal Horticultural Society at London, England.

THE PLANT

Origin: Seedling.

Parentage:

*Seed parent.*—Variety No. 76 MB 15 (unpatented).

*Pollen parent.*—Variety No. 70 V 43 (unpatented).

Classification:

*Botanic.*—*Dianthus caryophyllus.*

*Commercial.*—Spray carnation.

Form: Bush with at least four stems emitted near the ground.

Height: About 108 cm., in average, at eight months of growth.

Main stem length: Less than 15 cm. due to pinching.

Branching character: Very branched.

Growth habit: Vigorous, upright and rigid.

Foliage:

*Quantity.*—Very abundant with more than 120 leaves.

*Leaf size.*—About 13.1 cm. long and 0.9 cm. wide, at the seventh node.

*Leaf shape.*—Oblong with entire margins.

*Texture.*—Leathery.

*Ribs and Veins.*—Hardly noticeable.

*Rachis.*—Hardly noticeable.

*Color.*—Both upper side and under side, 189-A.

THE BUD

Size: Medium.

*Average diameter.*—About 1.4 cm.

*Average length.*—About 2.8 cm.

Form: Long cylindrical.

Opening rate: Normal.

Color of petals: When sepals first divide and when petals begin to unfurl, 65-C.

Sepals:

*Number.*—Five.

*Shape.*—Generally ovate but joined together at the lower portions and having an acuminate apex.

*Character.*—Hooded over the bud and curled back when the flowers open.

*Color.*—Inside, 144-C. Outside 143-C and 145-A.

*Striae.*—Longitudinal.

Calyx:

*Shape.*—Cylindrical.

*Splitting.*—The calyx does not split.

*Aspect.*—Smooth.

Flower stem:

*Character.*—Erect and rigid.

*Color.*—189-A.

THE INFLORESCENCE

Blooming habit: Recurrent and profusely during Spring, midseason and Fall blooming periods with a tendency to give few blooms in the Fall.

Size of bloom: Medium.

*Diameter.*—Averages about 6.5 cm.

*Depth.*—Averages about 5.4 cm.

Borne: In a cluster.

Shape: When bloom first opens, a somewhat higher center. When bloom matures, lightly dome-shaped.

Petalage:

*Number of petals.*—Averages about thirty-one.

*Arrangement.*—Imbricated.

*Form.*—Fan-shaped with repand margins with a very little serrated apex.

*Texture.*—Leathery.

*Aspect.*—Satiny.

*Color.*—Both outer and inside petals: Body — Generally 65-C with a central portion of 65-B and a greenish base. Reverse side — 65-C.

Petaloids:

*Number.*—Less than five.

*Size.*—Smaller than the petals.

*Color.*—The same as the petals.

Flower stem:

*Length.*—Averages about 58.9 cm. cut at the tenth node.

*Color.*—189-A.

*Character.*—Strong and upright.

Discoloration after full bloom: Very slight.

Persistence: The flowers hang on and dry.

Fragrance: Perceptible.

Diease resistance: Very resistant to *Fusarium oxysporum* as observed I.N.R.A. 06600 Antibes, France.

Lasting Quality: At least ten days as a cut flower in vase keeping.

REPRODUCTIVE ORGANS

Stamens:

*Number.*—Seven to eleven.

*Arrangement.*—Around the ovary.

*Anthers.*—Size: About 4 mm. Color: Whitish.

Pistils:

*Number.*—Two.

*Styles.*—Length: About 1.7 cm. Color: Whitish.

*Stigma.*—Color: Whitish.

Character of Ovaries: Ribbed.

The new variety of spray carnation somewhat resembles the variety 'Londrino' (U.S. Plant Pat. No. 3,570) but is distinguished by having a longer stem, a plain and paler color, a larger flower and round flower petals.

The characteristics of this new plant can be more-or-less modulated according to the environmental conditions as observed in Spring in the southern part of France.

We claim:

1. The new and distinct spray carnation cultivar and the parts thereof, substantially as herein shown and described, characterized in particular by the light purple coloration of its flowers, which are produced profusely at several times during the year, the plant having a vigorous growth habit with abundant foliage and good resistance to *Fusarium oxysporum.*

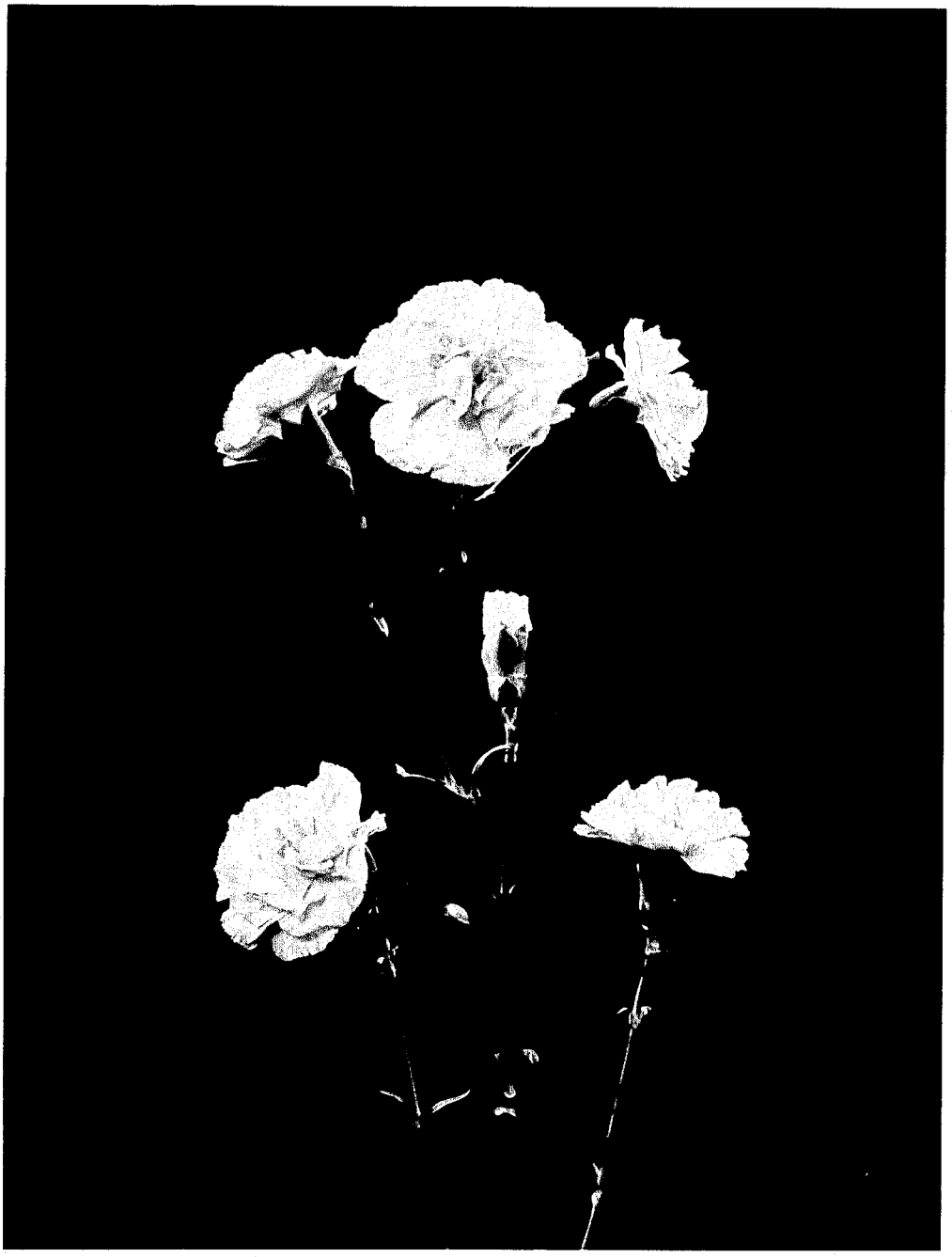

* * * * *